United States Patent [19]

Kojima et al.

[11] Patent Number: 4,833,089
[45] Date of Patent: May 23, 1989

[54] PRESSURE INCUBATOR

[75] Inventors: Kiyotsugu Kojima; Kouiichi Yamagata, both of Kyoto, Japan

[73] Assignee: Shimadzu Corporation, Kyoto, Japan

[21] Appl. No.: 95,907

[22] Filed: Sep. 14, 1987

[30] Foreign Application Priority Data

Sep. 19, 1986 [JP] Japan .................. 61-223434
Jul. 27, 1987 [JP] Japan .................. 62-189829

[51] Int. Cl.$^4$ .................................................. C12M 1/04
[52] U.S. Cl. ................................ 435/313; 435/316; 435/291; 435/284
[58] Field of Search ............... 435/313, 311, 284, 286, 435/287, 291, 296, 315, 316

[56] References Cited

U.S. PATENT DOCUMENTS 4,513,280 4/1985 Hannan et al. ............... 435/316 X
4,673,650 6/1987 Braden ........................... 435/316 X
4,686,188 8/1987 Whitley ............................. 435/313

Primary Examiner—Larry Jones
Attorney, Agent, or Firm—Sheldon Palmer

[57] ABSTRACT

A pressure incubator comprising a control system for supplying oxygen to the culture vessel in the space above the medium therein to hold the interior of the vessel pressurized with oxygen and give an increased oxygen partial pressure, which incubator is useful for incubating cells or aerobic microorganisms in vitro to a high density.

4 Claims, 2 Drawing Sheets

PRESSURE INCUBATOR

BACKGROUND OF THE INVENTION

1. Field of the Invention

The present invention relates to a pressure incubator, and more particularly to a pressure incubator used for incubating cells or aerobic microorganisms in vitro to a high density.

2. Description of the Prior Art

In order to incubate cells or aerobic microorganisms in vitro to a high density, it is necessary to supply a sufficient amount of oxygen to the medium in a culture vessel and to fully replace the medium in order to remove the waste matter produced in the medium and to replenish the medium with nutrients. To meet the first requirement, there is an apparatus known for incubating cells at atmospheric pressure in the presence of hemoglobin, fluorocarbon or the like and which is capable of dissolving oxygen in an amount 20 times the amount soluble in water as an $O_2$ carrier (Yukio Sugino, "Cell Incubation Techniques," Kohdansha, 1985, p. 133). Also known is an apparatus which comprises a tube for introducing gaseous oxygen into the space above the culture medium or into the medium within a culture vessel to bring the gas into contact with the medium or bubble the gas through the medium at atmosphere pressure. To meet the second requirement, the cells must be separated from the culture by directly filtering the cell-containing or by using a cell sedimentation tube utilizing the fact that the cells have a greater specific gravity than the medium (the same publication as above, p. 148).

However, when an additional substance is incorporated into the medium, there arises a need to resort to a cumbersome procedure for collecting the product from the medium and isolating the product in a purified form, while the result achieved by the supply of oxygen gas into the space above the medium is dependent on the speed of agitation of the medium. The introduction of oxygen gas into the medium is efficient, but excess bubbles in the medium destroy the cells. Thus, the above apparatus or methods each have different problems associated with them.

On the other hand, direct filtration of the culture to separate the cells from the medium rapidly clogs the filter, which is therefore not usable for a prolonged period of time, while the cell sedimentation tube must be used at a uniform ambient temperature. Otherwise, convection will occur, making it impossible to separate the cells from the medium. Further because the quantity of medium that can be separated off is limited by the settling rate of cells, high-density incubation encounters the problem that the medium can not be changed as frequently as is desired.

One object of the present invention, which has been accomplished in view of the foregoing situation, is to provide a pressure incubator wherein oxygen gas can be supplied to the culture efficiently using no additive and without destroying the cells. Another object of the invention is to provide a pressure incubator which is so adapted that the medium in a culture vessel can be fully replaced.

SUMMARY OF THE INVENTION

Accordingly, the present invention provides a pressure incubator which comprises a closable culture vessel for containing a medium for incubating cells or aerobic microorganisms, an oxygen supply channel communicating with an upper space within the culture vessel for supplying oxygen from an oxygen source to the culture vessel via a flow regulator, an exhaust channel similarly communicating with the interior of the culture vessel for discharging a gas from the culture vessel via an exhaust regulator, means for stirring the medium within the culture vessel, means for detecting the concentration of oxygen dissolved in the medium, and a control unit for maintaining the interior of the culture vessel in a state pressurized with oxygen by controlling the regulators in accordance with the detection output of the detecting means.

The invention further provides a pressure incubator of the type described above and which further comprises medium supply means for replenishing the culture vessel with a fresh medium, a culture recycling channel, and culture filtration means provided at an intermediate portion of the recycling channel and comprising a filter tube permitting passage of the dissolved components of the medium but not permitting passage of cells or the like.

The incubator of the invention is characterized in that it comprises a control system for supplying oxygen to the culture vessel in the space above the medium therein to keep the interior of the vessel pressurized with oxygen and give an increased oxygen partial pressure, whereby oxygen is forcibly dissolved in the medium to increase the dissolved oxygen concentration of the medium without aerating the medium or without adding to the medium any substance for the supply of oxygen, the control system being operable to supply oxygen to the culture vessel in accordance with a reduction in the dissolved oxygen concentration of the medium to keep the medium pressurized with oxygen and thereby maintain the oxygen concentration within a specified range.

The incubator of the invention is further characterized by medium replacing means comprising a channel for recycling the culture through the pressure culture vessel while releasing the solutes of the medium from the recycling channel, and means for replenishing the vessel with a fresh medium, whereby the medium within the vessel can be replaced efficiently.

According to the present invention, oxygen is forcibly dissolved in the medium under pressure for the medium to retain at least a specified preselected dissolved oxygen concentration at all times, so that cells or aerobic microorganisms can be incubated to a higher density than heretofore possible. Consequently, an increased quantity of cell product can be collected from a small amount of culture. Further because there is no need to add to the medium any substance for the supply of oxygen, the cell product can be collected, separated off and purified with ease. The incubator further permits repeated replacement of the medium over a prolonged period of time efficiently, consequently assuring high-density incubation over a long period of time. The incubabor is also usable as a bioreactor.

DESCRIPTION OF THE PREFERRED EMBODIMENTS

Figure 1:
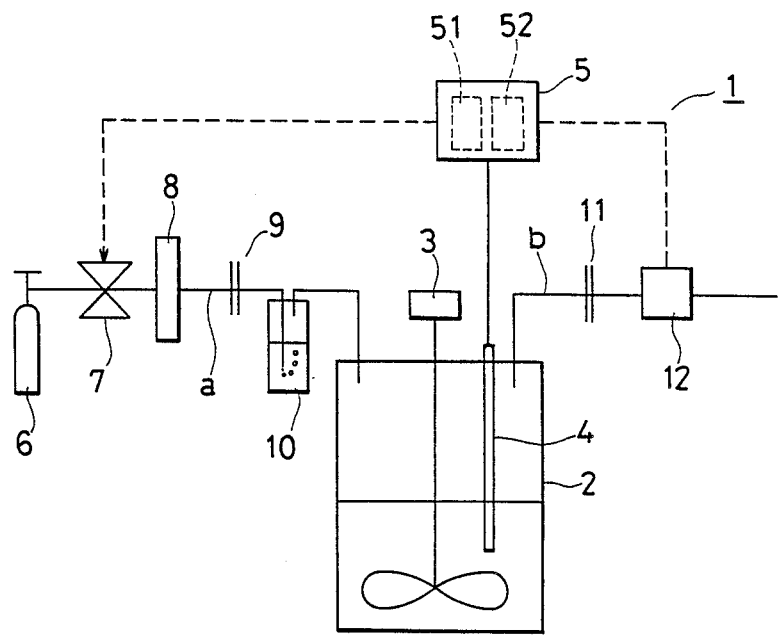
FIG. 1 is a diagram showing the construction of a pressure incubator embodying the invention.

The apparatus of the present invention is adapted to incubate cells or aerobic microorganisms (hereinafter referred to as "cells") to a high density.

The cells to be incubated by the apparatus of the invention are basically any animal cells, suitably cells derived from mammals, for example, mouse hybridoma, human lymphatic cells NAT-30, etc. However, cells of fishes and insects which are to be incubated at low temperatures (up to 30° C.) are not suitable. Although not limitative, examples of microorganisms that can be incubated by the present apparatus are staphylococci, streptococci, pneumococci, gonococci, meningococci, *Pseudomonas aeruginosa, Pseudomonas mallei, Bordetella pertussis,* the genus Brucella, *Francisella tularensis, Legionella pneumophila, E. coli,* the genus Salmonella, the genus Shigella, *Vibrio cholerae, Vibrio parahaemolyticus,* lactobacilli, *Bacillus bifidus, Corynebacterium diphtheriae,* mycoplasmas, fungi, etc.

The culture vessel for use in the incubator of the invention preferably comprises a container for a medium and a closure removably attached to the container for closing the container. It is therefore desirable that the specified members and channel members to be attached to the culture vessel be provided on the closure. In this case, the specified members and channel members are so attached to the closure that the closure can be kept hermetically sealed.

The oxygen supply channel for use in the incubator of the invention is provided in communication with a space within the culture vessel and communicates with an oxygen source via a flow regulator. A high-pressure oxygen cylinder, or when desired, a compressor or the like is used as the oxygen source so as to maintain the interior of the culture vessel pressurized with the supplied oxygen. The flow regulator is adapted to close the channel or to adjust the rate of flow of oxygen gas through the channel. For example, an electromagnetic valve, needle valve or the like is used as the regulator. The oxygen supply channel may be provided with an antiseptic, or sterile filter, or the like.

The exhaust channel for use in the present incubator is in communication with the space within the culture vessel. The exhaust channel is equipped with an exhaust regulator for closing the channel or adjusting the amount of gas to be discharged therethrough. For example, an electromagnetic valve, needle valve or the like is used as the regulator. The exhaust channel may be made to merely extend into a drain or other waste disposal.

The stirring means can be any device, so long as it is capable of giving a uniform dissolved oxygen concentration to the medium or culture. To assure agitation without destroying cells while permitting the culture vessel to retain a constant internal pressure, it is desirable to use a magnetic stirrer or mechanical means having stirring blades or the like.

The means for detecting the concentration of dissolved oxygen is preferably a dissolved oxygen electrode (DO sensor). This device is connected to the control unit to be described.

The control unit is provided with a memory for storing a predetermined dissolved oxygen concentration and a comparator for comparing the stored value with the concentration value detected by the detecting means and is adapted to operate the flow regulator on the oxygen supply channel, the exhaust regulator on the exhaust channel and the oxygen source based on an output signal from the comparator. The predetermined concentration value to be stored in the memory is preferably about 5 ppm although slightly variable depending on the oxygen demand of the cells to be incubated. When the concentration measurement is found by the comparator to be less than the stored value, the control unit closes the flow regulator and the exhaust regulator in response to the signal from the comparator and thereafter actuates the oxygen source. When a compressor is used as the oxygen source, the compressor is operated in response to the signal from the comparator. Consequently, the interior of the culture vessel is pressurized with oxygen. Preferably, this pressure is about 0.3 to about 0.7 kg/cm$^2$ in corresponding relation to the stored concentration value.

The culture vessel of the present incubator may be provided with a culture recycling channel having filtration means, and medium supply means. The recycling channel and the medium supply means constitute medium replacing means. The filtration means provided in the recycling channel primarily comprises a filter tube permitting passage of the dissolved components of the medium therethrough but not permitting passage of cells. Stated more specifically, the filtration means preferably comprises a so-called cross-flow filter having a filtration surface disposed coaxially with the recycling channel and capable of releasing the permeable components from the recycling channel outside while the culture is recycled through the channel. Preferably, the filtration means is provided removably in the recycling channel. More preferably, the said filter tube is made of a ceramic material.

The recycling channel includes liquid transport means which is preferably a peristaltic pump or the like.

The medium supply means comprises a medium container, and a medium transport channel extending from the container to the culture vessel via a liquid transport means which is preferably a peristaltic pump or the like. While the medium supply means is operated when the amount of medium in the culture vessel decreases to less than a specified quantity, it is preferable to automatically control the operation. For this purpose, an automatic control system is desirable for operating the liquid transport means in accordance with the variation of the liquid level of the medium or culture in the culture vessel. For example, such a system comprises a liquid level sensor disposed in the culture vessel for controllably driving or stopping the liquid transport means in response to the output signal from the sensor.

When required, the incubator of the present invention may further include a carbon dioxide supply channel and an air introduction channel for the culture vessel. The supply of carbon dioxide is needed for inhibiting the variation of the pH of the culture toward basicity, while the introduction of air is necessary to decrease the oxygen concentration of the culture within the vessel when excess oxygen supplied would prove to be detrimental to the cells. The carbon dioxide supply channel and the air introduction channel are each provided with a regulator and may be provided independently or in combination with the oxygen supply channel.

The culture vessel of the invention may be provided with conventional means for measuring the pH of the culture and for controlling the temperature of the same.

According to the present invention, the interior of the culture vessel can be maintained pressurized with oxygen to cause oxygen gas to be forcibly dissolved in the medium or culture and to give the culture at least a specified dissolved oxygen concentration at all times, so that cells or aerobic microorganisms can be incubated to a high density. With the culture circulated through the recycling channel equipped with filtration means, the solutes in the culture are released from the recycling channel outside thereof, while the cells remaining in the channel on separation are returned to the culture vessel by the flow through the recycling channel. The culture vessel which is replenished with a fresh medium by the medium supply means thus retains a specified amount of medium therein.

The invention will be described in detail with reference to the following embodiments, which are not intended limit the invention.

Embodiment 1

FIG. 1 is a diagram showing one embodiment of a pressure incubator according to the invention. Referring to this diagram, the incubator 1 comprises a culture vessel 2, sirrer 3, DO sensor 4, control unit 5, oxygen supply channel a and exhaust channel b.

The culture vessel 2 has closable medium inlet and outlet (not shown) and is equipped with the stirrer 3. The stirrer stirs the medium to render the medium uniform in dissolved oxygen concentration.

The oxygen supply channel a extends from an oxygen cylinder 6 to the culture vessel 2 via an electromagnetic valve 7, flow meter 8, antiseptic, or sterile filter 9 and scrubbing bottle 10 in the order mentioned. The exhaust channel b is in communication with the vessel 2 by way of an electromagnetic valve 12 and antiseptic filter 11.

The control unit 5 has a memory 51 and a concentration comparator 52. The memory 51 stores a predetermined dissolved oxygen concentration, while the comparator 52 is connected to the DO sensor 4 and compares the dissolved oxygen concentration measured by the DO sensor with the stored concentration. In accordance with the signal from the comparator 52, the control unit 5 opens or closes valve 7 in channel a or valve 12 in channel b The incubator operates in the following manner.

First, the dissolved oxygen concentration at which the medium is to be set is stored in the memory of the control unit. A medium containing cells or aerobic microorganisms is placed into the culture vessel and stirred. In this state, the electromagnetic valves on the oxygen supply channel and the exhaust channel are both opened to pass oxygen through the space in the vessel in contact with the medium. The valves are then closed to initiate incubation in this state. During incubation, the dissolved oxygen concentration measured by the DO sensor placed in the medium is compared with the stored predetermined concentration valve by the comparator of the control unit. As the incubation proceeds in this state, the oxygen dissolved in the medium is consumed by the cells or aerobic microorganisms. Consequently, the concentration measurement by the DO sensor drops below the pre-selected stored value, whereupon the electromagnetic valves on the oxygen supply channel and the exhaust channel are opened, permitting the oxygen cylinder to supply oxygen onto the surface of the culture. As the incubation is further continued in this state, the density of cells or aerobic microorganisms increases, consuming the dissolved oxygen at a higher rate, with the result that it becomes no longer possible to maintain the stored concentration value merely by supplying oxygen onto the surface of the culture in the above manner. In this state, the dissolved oxygen concentration of the culture measured by the DO sensor is below the stored value. The control unit then operates to close only the valve on the exhaust channel to pressurize the interior of the culture vessel with the supplied oxygen, forcibly dissolving oxygen in the culture to give an increased dissolved oxygen concentration. The cells or microorganisms are further incubated to a higher density.

Embodiment 2

Figure 2:
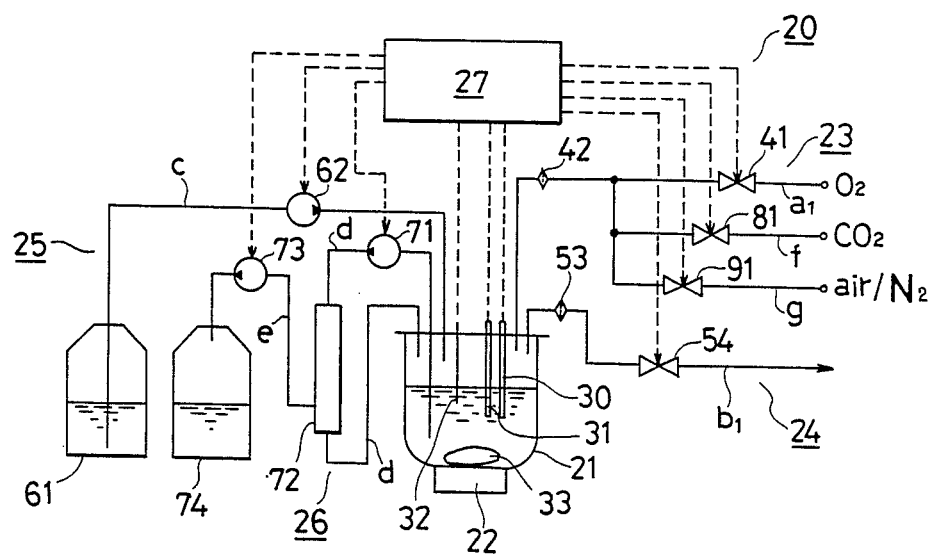
FIG. 2 is a diagram showing the construction of another pressure incubator embodying the invention.

FIG. 2 is a diagram showing another pressure incubator 20 embodying the invention. With reference to the diagram, the incubator 20 primarily comprises a culture vessel 21, stirring means 22, oxygen supply means 23, exhaust means 24, medium supply means 25, culture filtration means 26 and control unit 27.

The culture vessel 21 comprises a medium container and a closure for movably closing the container. The closure is provided, in specified positions, with a DO sensor 30, pH electrode 31, liquid level sensor 32 and channel members for providing the channels to be described below. The culture vessel is further provided with a temperature controller (not shown) for maintaining the medium at a constant level.

A magnetic stirrer is used as the stirring means 22 and has a rotor 33. The medium is stirred by the stirring means 22 and thereby made uniform with respect to dissolved oxygen concentration.

The oxygen supply means 23 comprises an oxygen supply channel a1 extending from an oxygen cylinder (not shown) to the closure of the culture vessel 21 via an electromagnetic valve 41 and then via an antiseptic filter 42. The channel a1 is in communication with an upper space within the culture vessel. This channel may be provided with a scrubbing bottle between the valve 41 and the filter 42. The flow rate of oxygen is adjusted by a flow meter attached to the cylinder.

The exhaust means 24 comprises an exhaust channel b1 in communication with the upper space in the culture vessel 21 through the closure and extending to an exhaust outlet (not shown) via an antiseptic filter 53 and then via an electromagnetic valve 54.

The medium supply means 25 comprises a medium container 61 containing fresh medium, and a medium supply channel c communicating with container 61 in the vicinity of its bottom, extending therefrom to the culture vessel 21 via peristaltic pump 62 and communicating with the interior upper space of the culture vessel through its closure.

The culture filtration means 26 comprises a culture recycling channel d communicating with the interior of the culture vessel 21 in the vicinity of its bottom through the closure, extending therefrom via a peristaltic pump 71 and then via a filter unit 72 to the vessel 21 again and communicating with the interior upper space thereof through the closure. A cross-flow filter is used as the filter unit 72. More specifically, a filter tube having a tubular filtration surface is inserted in the recycling channel d, whereby the filtration surace is positioned coaxially with the channel. A tubular outer container is provided around the filter tube for accommodating the filtrate. The filter tube is replaceable. A filtrate discharge channel e extends from the filter unit 72 to a medium collection tank 74 via a peristaltic pump 73.

Indicated at f is a carbon dioxide supply channel extending from a carbon dioxide cylinder (not shown)

to the oxygen supply channel a1 via an electromagnetic valve 81, and at g an air/N₂ introduction channel extending from an air/N₂ cylinder (not shown) to the channel a1 via an electromagnetic valve 91.

The control unit 27 is electrically connected to the DO sensor 30, pH electrode 31, liquid level sensor 32, electromagnetic valves 41, 52, 81, 91 and peristaltic pumps 62, 71, 73 for controlling the operation of these valves and pumps. The control unit 27 primarily comprises a system for controlling the dissolved oxygen concentration of the culture and a system for controlling the replacement of the medium. The dissolved oxygen concentration control system has a memory for storing a predetermined value of dissolved oxygen concentration, and a concentration comparator for comparing the dissolved oxygen concentration measured by the DO sensor with the stored value. In accordance with a signal from the comparator, the system opens or closes the valve 41 on the oxygen supply channel a1 and the valve 52 on the exhaust channel b1. The medium replacement control system is adapted to operate the peristaltic pump 62 of the medium supply means for a specified period of time in response to a signal from the liquid level sensor 32.

Next, the operation of the incubator will be described.

First, the dissolved oxygen concentration at which the medium is to be set is stored in the memory of the control unit. Next, a medium containing cells or aerobic microorganisms is placed into the culture vessel and stirred. In this state, the electromagnetic valves on the oxygen supply channel and the exhaust channel are both opened to pass oxygen over the medium in contact therewith. The valves are then closed to initiate incubation in this state. During incubation, the dissolved oxygen concentration measured by the DO sensor placed in the medium is compared with the stored predetermined concentration value by the comparator of the control unit. As the incubation proceeds in this state, the oxygen dissolved in the medium is consumed by the cells or aerobic microorganisms. Consequently, the concentration measurement by the DO sensor drops below the stored value, whereupon the valves on the oxygen supply channel and the exhaust channel are opened, permitting the oxygen cylinder to supply oxygen onto the surface of the culture. As the incubation is further continued in this state, the density of cells or aerobic microorganisms increases, consuming the dissolved oxygen at a higher rate, with the result that it becomes no longer possible to maintain the stored concentration value merely by supplying oxygen onto the culture surface in the above manner. In this state, the dissolved oxygen concentration of the culture measured by the DO sensor is below the stored value. The control unit then operates to close only the valve on the exhaust channel to pressurize the interior of the culture vessel with the supplied oxygen, forcibly dissolving oxygen in the culture to give an increased dissolved oxygen concentration. The cells or microorganisms are further incubated to a higher density.

On the other hand, the peristaltic pump on the culture recycling channel is operated in response to an instruction from the control unit, whereby the culture in the culture vessel is circulated through the channel. During the circulation, waste matter dissolved in the medium and dissolved components of the medium permeate through the filter tube of the filter unit in the recycling channel and released outside the channel. The incubated cells separated off and remaining in the channel are returned to the culture vessel as entrained in the flow through the channel. The released solutes are transferred to the medium collection tank by the operation of the peristaltic pump on the filtrate discharge channel. The operation of the filter decreases the quantity of the medium in the culture vessel, lowering the liquid level off the liquid level sensor, whereupon the sensor is brought out of conduction. This produces a liquid level detection signal, which is fed to the control unit. In accordance with the value of the output signal, the control unit operates the peristaltic pump of the medium supply means for a predetermined period of time, whereby a specified quantity of fresh medium is supplied to the culture vessel for higher-density incubation.

Figure 3:
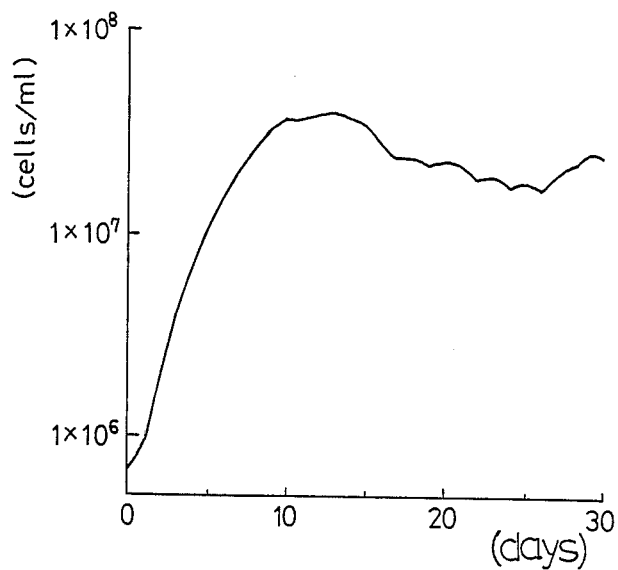
FIG. 3 is a graph showing the relation between incubation time and cell density, as determined by incubating human lymphatic cells in the apparatus of FIG. 2.

FIG. 3 shows the result achieved by incubating human lymphatic cells NAT-30 using the incubator of FIG. 2 under the following conditions.

Amount of medium: 500 ml.
Medium: RDF medium supplemented with bovine serum albumin, insulin, transferrin, ethanolamine and sodium selenite.
Incubation conditions: temperature 37° C., speed of rotation of stirrer 60 r.p.m., DO concentration 5.0 ppm, pH 7.2.
Medium replacement rate: 1.0 liter/day.
Filter tube: ceramic filter 10 μm in pore size, 10 mm in outside diameter, 7 mm in inside diameter, 200 mm in length.

The results shown in FIG. 3, reveal that high-density incubation can be carried out by the incubator of the invention over a prolonged period of time and after a relatively short start-up time.

What is claimed is:

1. A pressure incubator comprising a closable culture vessel for containing a medium for incubating cells or aerobic microorganisms, an oxygen supply channel provided with a flow regulator for supplying oxygen from an oxygen source to the culture vessel via the flow regulator, an exhaust channel provided with an exhaust regulator for discharging a gas from the culture vessel via the exhaust regulator, means for stirring the medium within the culture vessel, means for detecting the concentration of oxygen dissolved in the medium, and a control unit for maintaining the interior of the culture vessel in a state pressurized with oxygen by controlling the flow and exhaust regulators in accordance with the detection signal of the detecting means, the oxygen supply channel being adapted to communicate with a space above the medium in the culture vessel so as not to substantially bubble the medium with the oxygen supplied therethrough, the exhaust channel being adapted to communicate with the space.

2. A pressure incubator as defined in claim 1 wherein the control unit comprises a memory for storing a predetermined concentration of dissolved oxygen and a comparator for comparing the predetermined stored concentration value with the concentration value measured by the detecting means, said control unit being operative to provide an operation instruction to the oxygen source, the flow regulator and the exhaust regulator so as to supply oxygen to the culture vessel when the measured concentration value and to hold the interior of the vessel pressurized with oxygen until the dissolved oxygen concentration of the medium becomes equal to or higher than the stored concentration value.

3. A pressure incubator as defined in claim 1 wherein the culture vessel is provided with medium supply means for replenishing the vessel with fresh medium and a culture recycling channel, the recycling channel being provided at an intermediate portion thereof with culture filtration means comprising a filter tube permitting passage of the dissolved components of the medium therethrough but not permitting passage of cells or the like therethrough.

4. A pressure incubator as defined in claim 1 wherein the oxygen supply channel has joined thereto at least one of a carbon dioxide supply channel and an air introduction channel.

* * * * *